United States Patent [19]

Simon

[11] Patent Number: 4,883,053

[45] Date of Patent: Nov. 28, 1989

[54] SELF-SUPPORTING ANGULATOR DEVICE FOR PRECISE PERCUTANEOUS INSERTION OF A NEEDLE OR OTHER OBJECT

[75] Inventor: Morris Simon, Boston, Mass.

[73] Assignee: Beth Israel Hospital, Boston, Mass.

[21] Appl. No.: 339,916

[22] Filed: Apr. 17, 1989

Related U.S. Application Data

[63] Continuation of Ser. No. 98,142, Sep. 18, 1987, abandoned.

[51] Int. Cl.⁴ .............................................. A61B 17/00
[52] U.S. Cl. ...................... 128/303 B; 128/DIG. 26; 604/116; 604/180
[58] Field of Search ............... 604/116, 177, 174, 180, 604/175, 178; 128/303 B, DIG. 26

[56] References Cited

U.S. PATENT DOCUMENTS

| | | | |
|---|---|---|---|
| 2,451,183 | 10/1948 | Tantimonaco | 128/303 B X |
| 2,697,433 | 12/1954 | Zehnder | 128/303 B X |
| 3,288,137 | 11/1966 | Lund | 604/180 X |
| 4,638,798 | 1/1987 | Shelden et al. | 128/303 B |
| 4,733,661 | 3/1988 | Palestrant | 128/303 B |

Primary Examiner—Michael H. Thaler
Attorney, Agent, or Firm—David Prashker

[57] ABSTRACT

A novel angulator device is provided for precise aiming, holding and percutaneous insertion of an object such as a needle into the tissues of a subject. The device is erectable, self-supporting, and collapsable at will. The preferred embodiments are composed of flexible materials which are presterilized, disposable, and directly attachable to the skin of the subject using adhesives. The angulator device provides security, accuracy, and convenience to surgeons, radiologists and other physicians performing a variety of operative procedures including tissue biopsy and aspiration of fluid collections.

8 Claims, 5 Drawing Sheets

SELF-SUPPORTING ANGULATOR DEVICE FOR PRECISE PERCUTANEOUS INSERTION OF A NEEDLE OR OTHER OBJECT

This application is a continuation of application Ser. No. 098,142, filed September 18, 1987 now abandoned.

FIELD OF THE INVENTION

The present invention is concerned with holding and guiding instruments and devices used by physicians and surgeons to localize specific anatomical sites or diseased tissues in the body and is particularly directed to angulator devices for the precise positioning and percutaneous insertion of needles and wires and catheters for biopsy examination and aspiration purposes.

BACKGROUND OF THE INVENTION

In many clinical situations, before a proper diagnosis can be made and effective therapy instituted, it is necessary to identify a localized focus of disease deep within specific organs or tissues in the body; obtain a sample of tissue from the diseased region; and evaluate it histologically. Typical examples are the presence of a small mass in the breast of a woman or a nodule in the lung. In order to accurately diagnose and then effectively treat the disease, the breast mass or lung nodule, it often becomes necessary for a surgeon to excise a portion of the diseased tissue for microscopic examination and analysis. Thus, it is often necessary to insert long needles or wires, typically from four to eight inches in length, through the skin into the diseased region of the body, to include not only the breast or lung, but also deep seated organs such as the liver, kidney, and bony skeleton. Such needles are typically guided to their target tissue by any of a variety of imaging systems including X-ray fluoroscopy, computerized tomography, ultrasound, magnetic resonance and the like.

Generally, percutaneous insertion of objects such as needles, wires and catheters are employed to obtain biopsy specimens of the diseased tissues; drain abscesses; sample body fluids; and introduce medication or contrast agents into the body. The insertion of hollow needles, of various bore diameters and lengths, may also be the first step towards non-surgical placement of larger-bore catheters into the body of the subject by conventionally known means.

Precise positioning of the object to be surgically inserted, typically a small-bore needle, is simple in principle but is often difficult in practice. Initially, an appropriate and safe skin entry site is chosen; the site sterilized; and then infiltrated with a local anesthetic. The needle is then advanced into the tissues; its direction and depth checked repeatedly by one or more imaging systems; and adjustments made if necessary. The imaging system displays the internal target as well as the needle shaft and allows the surgeon to carefully aim the needle towards the target even though the target tissue may be small and deep seated. The ongoing and recurring problem, however, lies in the fact that it may be extremely difficult for the surgeon to maintain the needle at the exact angle required relative to the target tissue within the patient's body. In routine practice, the needle is inserted by hand and advanced part-way towards the estimated position of the target tissue site. The patient then is moved in and out of the viewing position of the particular imaging system to determine whether the needle is accurately aimed towards the target site; or whether the needle direction needs to be adjusted; and/or to determine how much further the needle should be advanced to reach the target tissue. This procedure may have to be repeated a number of times before completion.

The operator commonly improvises some support for the needle during this viewing period of time, often with a folded towel; or a stack of sterile swab pads; or some similar temporary arrangement, in order to maintain the needle in the inserted position until its relationship to the target tissue can be verified. This problem is compounded if the desired point of entry through the skin of the patient is on an oblique or vertical aspect of the body surface. It is often difficult to maintain the desired angle of entry in such instances and it is common for the surgeon to withdraw the needle and reinsert it at a different angle or aspect several times before the correct relationship to the target tissue is attained.

It is therefore commonly recognized that a device which would allow the surgeon to position a needle at the chosen skin entry site and to maintain the requisite angle of insertion into the tissue of the patient would be an extraordinarily useful and advantageous device. Such an article would not only allow for precise positioning of the needle to be inserted, but would also support the needle after initial insertion while its position within the body is being verified by the imaging system. It would also eliminate the requirement that the surgeon or surgical assistant physically grasp and maintain the inserted needle in position during the entirety of the verification procedure. Such a device would not only provide freedom, convenience and accuracy for the surgeon during the procedure, but also would provide greater comfort for the patient as well.

SUMMARY OF THE INVENTION

A self-supporting angulator for precise percutaneous insertion of an object into the body of a subject is provided, this angulator comprising a base plate; at least one primary member rotatably joined to the base plate; at least one secondary member rotatably joined to the base plate at an angle substantially radial to the axis of the primary member, this secondary member being positionable adjacent to the primary member at a plurality of different angles of intersection; means for coupling the rotatable secondary member to the rotatable primary member at a desired angle of intersection; and means for holding the object to be inserted disposed upon at least one of the rotatable members.

BRIEF DESCRIPTION OF THE FIGURES

The present invention may be more easily and fully understood when taken in conjunction with the accompanying drawing, in which.

DETAILED DESCRIPTION OF THE PREFERRED EMBODIMENTS

The present invention is an erectable and collapsable, self-supporting angulator device for the precise positioning, holding and percutaneous insertion of an object such as a needle into the tissues of the body. In preferred embodiments, the angulation device is provided as a compact, presterilized, biocompatible, and disposable article of manufacture which improves the accuracy of needle placement (and similar objects) for a variety of medical purposes. The angulation devices are compatible with all presently known imaging systems; are inexpensive; and substantially reduce both the operating time for and patient discomfort during the insertion procedure.

The preferred embodiment of the present invention is illustrated in a variety of different views and in both erected and collapsed states by FIGS. 1-7 respectively. The preferred design is shown in the folded or collapsed state by FIGS. 1 and 2 in which the angulator 10 comprises a semi-circular base plate 12, a short, arched primary member 14, and a longer, arched secondary member 16 positioned adjacent thereto. The base plate 12 is preferably formed of a flexible, resilient material which can be sterilized, is biocompatible, and disposable. It is usefully configured as a semi-circular disc 18 whose center has been perforated by an semi-oval shaped aperture 20. The primary member 14 is preferably arched in configuration from one end 22 to the other end 24 and is attached to the base plate 12 by rotatable joining means such as flexible hinges 26 and 28 respectively. While hinges 26, 28 are the preferred means of rotatable juncture, all joining means which allow the primary member 14 to rotate after being attached to the surface 18 of the base plate 12, regardless of specific position or mode of attachment, are suitable for use with the present invention.

Figure 1:
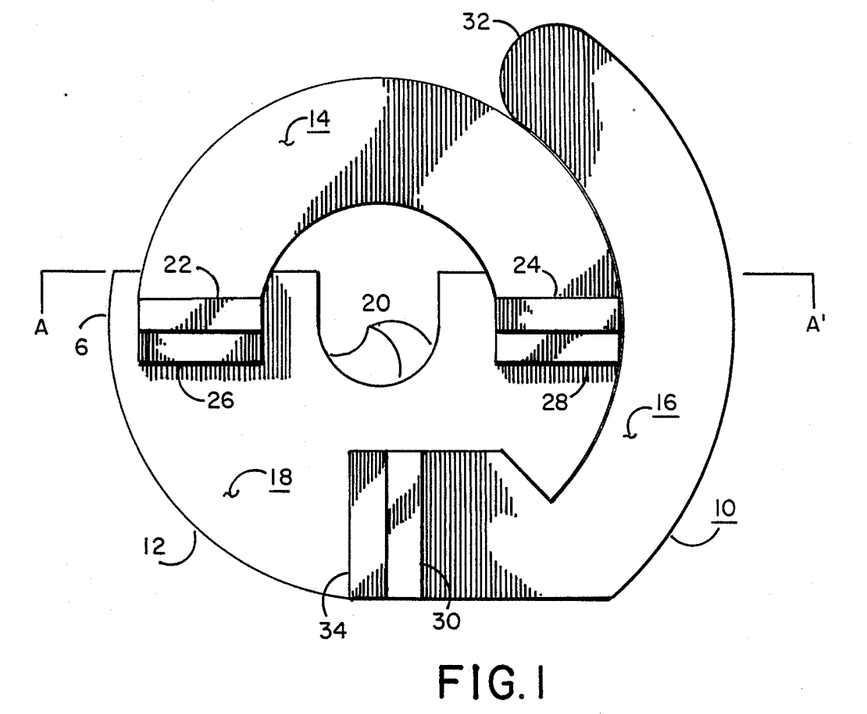
FIG. 1 is an overhead view of a preferred embodiment of an angulator device in a folded, collapsed state shown without a coupling bracket.
Figure 2:
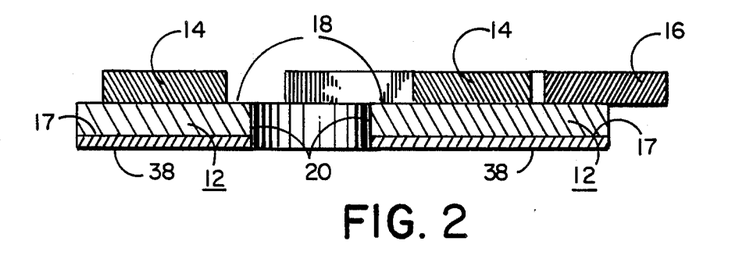
FIG. 2 is a cross-sectional view of the folded embodiment illustrated within FIG. 1 along the axis A A'.

The secondary member 16 is also preferably arched in configuration and desirably has a curvature parallel to the arched configuration of the primary member 14 such that two concentric arches are formed. The adjacent arched secondary member 16 has two ends 30 and 32, only one of which is rotatably joined to the base plate 12 at a location substantially radial to, and preferably at a right angle to, the axis of the primary member 14. As shown in FIGS. 1 and 2, the end 30 is rotatably joined to the surface of the semi-circular disc 18 via the flexible hinge 34. Other rotatable joining means for attaching the secondary member 16 to the base plate 12 may be substituted and employed as desired. It is also highly desirable that the underside 17 of the base plate 12 be coated with a non-toxic, biocompatible adhesive 38 as is illustrated in the cross-sectional view along the axis A A' of FIG. 2.

It will be noted and appreciated that while the primary member 14 and the secondary member 16 are preferably configured as concentric, arched elements, a variety of other shapes and configurations are also useful in varying degrees. Clearly, the members 14, 16 may alternatively be linear, sinusoidal, multisided with or without parallel sides, saw-toothed, or irregularly shaped—although these are generally considered to be less desirable than the simpler and more convenient arch configuration. Similarly, there is no requirement or necessity that either the primary member 14 or the secondary member 16 be comprised of a single construct or structure; to the contrary, each member may be composed of a plurality of elements joined together to form an integral unit. Morever, it is expected that a variety of different materials of varying tensile strength, flexibility, resiliency, and elasticity may be utilized to give one or more specific configurations which are deemed to be useful or necessary under specific conditions or test circumstances.

It will be noted also that there are no restrictions or limitations regarding the means of rotatably joining each primary member and secondary member to the surface of the base plate. Not only are the means for rotatably joining each member of no significant interest or value, but neither are the precise locations, dimensions, and proximate distant relationships of any meaningful concern to the invention as a whole. Since each primary member and secondary member may be configured in a variety of shapes, it is clear that the individual construction and configuration may provide one, two, or more ends by which to join the respective member to the surface of the base plate. Accordingly, so long as at least one end of a primary member is rotatably joined to the base plate and at least one end of a secondary member is also rotatably joined to the base plate, that embodiment is deemed to be within the scope and definition of the present invention.

The other criterion for all embodiments comprising this invention require: that the secondary member be positioned on the base plate at an angle substantially radial (and preferably 90°) to the axis of the corresponding primary member; and that the rotatably joined secondary member extend sufficiently in length to be positioned adjacent to the rotatable primary member at one, and preferably at a plurality of different angles of intersection. Thus, so long as the primary member and the adjacent secondary member are *not* substantially parallel to one another over the surface of the base plate, that positioning and construction will cause and angular intersection between the primary member and the secondary member sufficient to be within the definition of the present invention.

Figure 3:
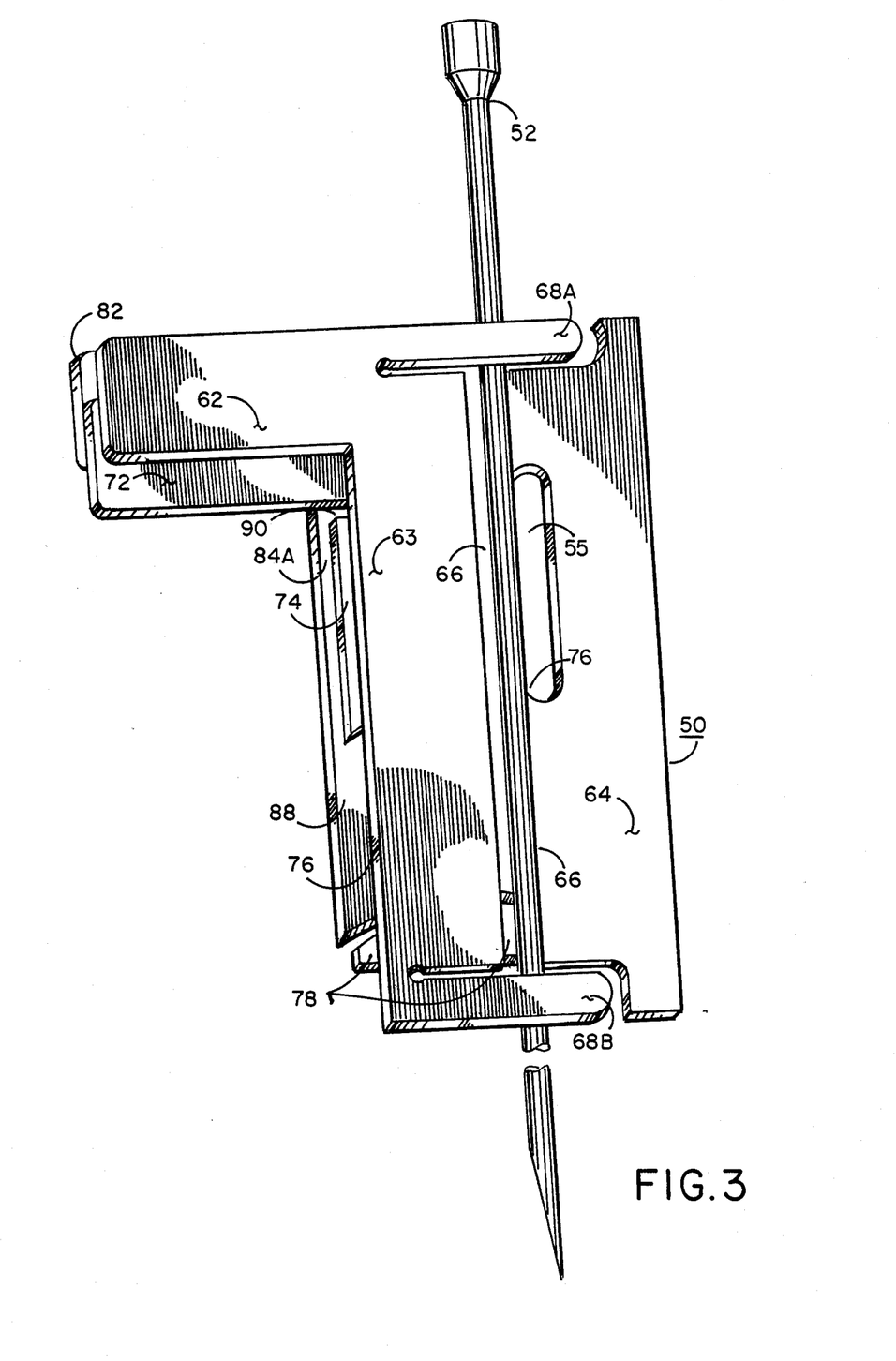
FIG. 3 is a perspective view of a preferred combined coupling bracket and needle holder comprising part of the present invention.
Figure 4A:
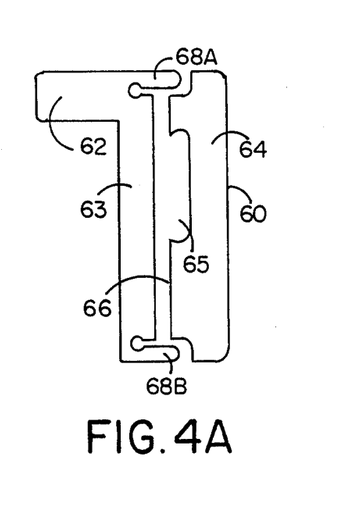
FIGS. 4a–4c are frontal views of the components comprising the coupling bracket and needle holder illustrated by FIG. 3.

The other component parts of the present invention include the means for coupling the rotatable secondary member to the rotatable primary member at a desired angle of intersection; and means for holding the object to be inserted (the needle) preferably along the common isocentric axis perpendicular to the intersection angle formed by the two rotatable members. In preferred embodiments of the present invention, the means for coupling the members and the means for holding the object to be inserted are combined into a signle article of manufacture such as appears in FIG. 3. As shown therein, a slidable, combined coupling bracket and object holder 50 is seen retaining an elongated needle 52. The preferred combined coupling bracket and needle holder 50 of FIG. 3 is preferably constructed as an integral unit from three components, a 2-part front plate, a 3-part middle plate, and a single part rear plate as appears in FIGS. 4a, 4b, and 4c respectively. The 2-part front plate 60 of FIG. 4a is substantially planar and is composed of an L-shaped arm section 62 and elongated center section 63, separated by a narrow space 66 from the other elongated half-section 64; a narrow slit 65; and a pair of clips 68a and 68b. The narrow space 66 between the half-section 63 and the half-section 64 forms a retention groove for the needle 52 or another object to be inserted.

Figure 4B:
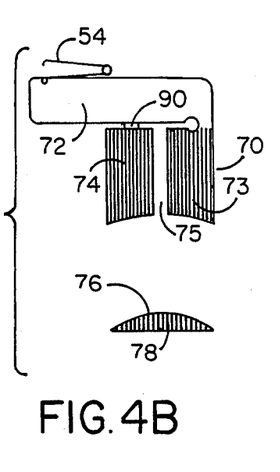

The middle plate 70 of FIG. 4b is a 3-part planar construction composed of an L-shaped arm portion 72 and fusable portion 73 separated by a short narrow slit 75 from the other fusable portion 74; an arched broad space 76; and a fusable curved support portion 78. The arched broad space 76 is an open channel configured to accommodate the width and thickness of the primary member 14 which is to be slid through the space 76 and maintained in place by the fusable curved support 78.

Figure 4C:
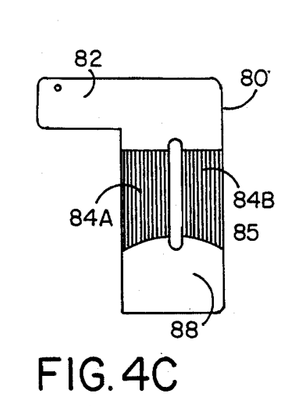

The rear plate 80 of FIG. 4c is also substantially planar and is composed of an L-shaped arm segment 82; two fusable segments 84a and 84b separated by a narrow slit 85; and a retaining segment 88.

Assembly of the unit is made by attaching the fusable segments 84a and 84b (by fusion, adhesive or other means) to the corresponding rear surfaces of fusable portions 74 and 73; which, in turn, are themselves joined on their front surfaces to the rear surfaces of portions 63 and 64 respectively. The curved support 78 is also joined to the rear surfaces of sections 63 and 64 towards their lower ends. If properly done, this mode of assembly for the 3-part middle plate 70 with respect to the 2-part front plate 60 and single part rear plate 80 causes the narrow slits 85, 75, and 65 to be in alignment—thereby forming a narrow slot 55 (of reduced length in the middle plane) through the entirety of the combined bracket and holder 50. In addition, it is preferred that a spring 54 be attached to both the L-shaped arm segment 82 and the L-shaped arm portion 72 to maintain a constant tension force between the respective parts. The properly aligned and assembled unit is the combined coupling bracket and object holder 50 illustrated by FIG. 3.

To assemble the angulator device 10, the combined coupling bracket and object holder 50 is mounted on the primary arched member 14 by tilting the retaining segment 88 backward to admit the primary member 14 into the arched broad space 76 of the middle plate 70. The primary member 14 is supported and held within the space 76 by the curved support 78 such that a sliding movement is facilitated. The free end of the secondary member 16 is then slid into the slot 55 of the coupling bracket 50. The spring tension thus locks arm 72 against the top edge of the secondary member 16; which in turn, is locked against the top edge of the primary member 14; which is pressed down onto the curved support 78.

The combined bracket and object holder 50 is constructed to be slidable over the entirety of the arched primary member 14 and/or the arched secondary member 16. Since the L-shaped arm segment 82 of the rear plate is directly aligned with the L-shaped arm section 62 of the front plate while the L-shaped arm portion 72 of the middle plate remains depressed by the spring tension, the application of a compression force (by finger pressure) between the outer L-shaped arms 82 and 62 above and the arm 72 below will cause a widening of the horizontal gap 90 between the upper and lower portions of the middle plate. This will release the tension between the L-shaped arm 72 of the middle plate against the secondary member 16; and the tension of the secondary member 16 against the primary member 14; and the tension of the primary member 14 against the curved support 78. This release of tension will free the primary and secondary members to be set at any desired angle relative to the base plate. Once the desired site on each member 14 and 16 is achieved, the compression force is removed and tension force restored by the spring 54 is sufficient to close the gap 90 between the upper and lower sections of the middle plate 70. The unit 50 is thus secured at this position on each of the members indefinitely.

Figure 5:
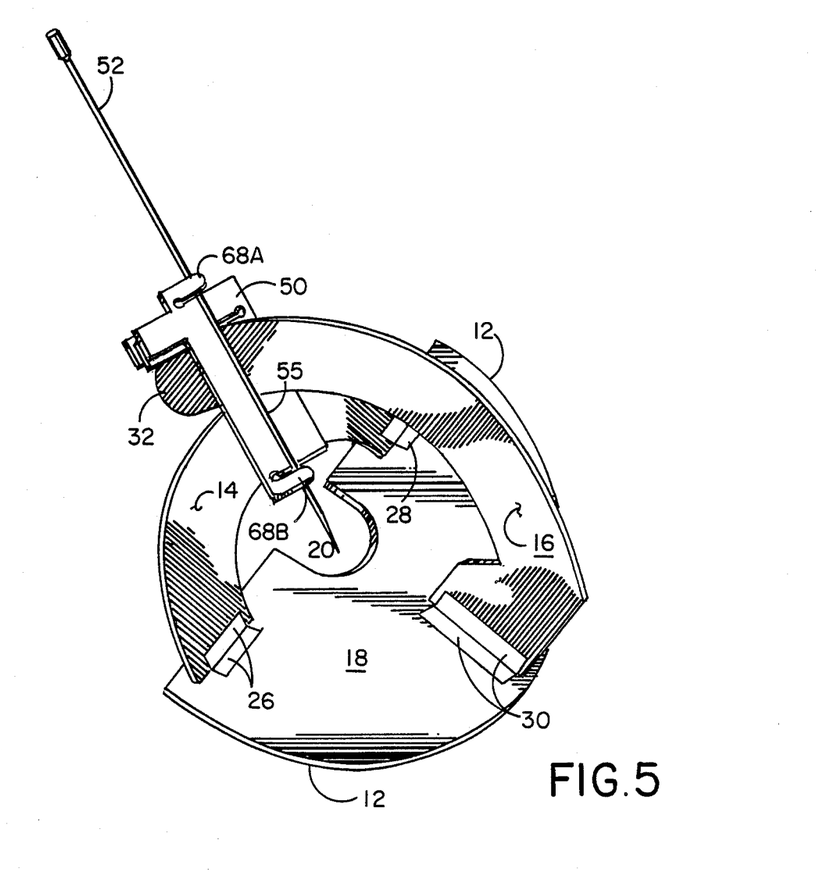
FIG. 5 is a perspective view of the preferred embodiment illustrated by FIGS. 1–5 in the fully erect, self-supporting state.
Figures 6, 7, 8:
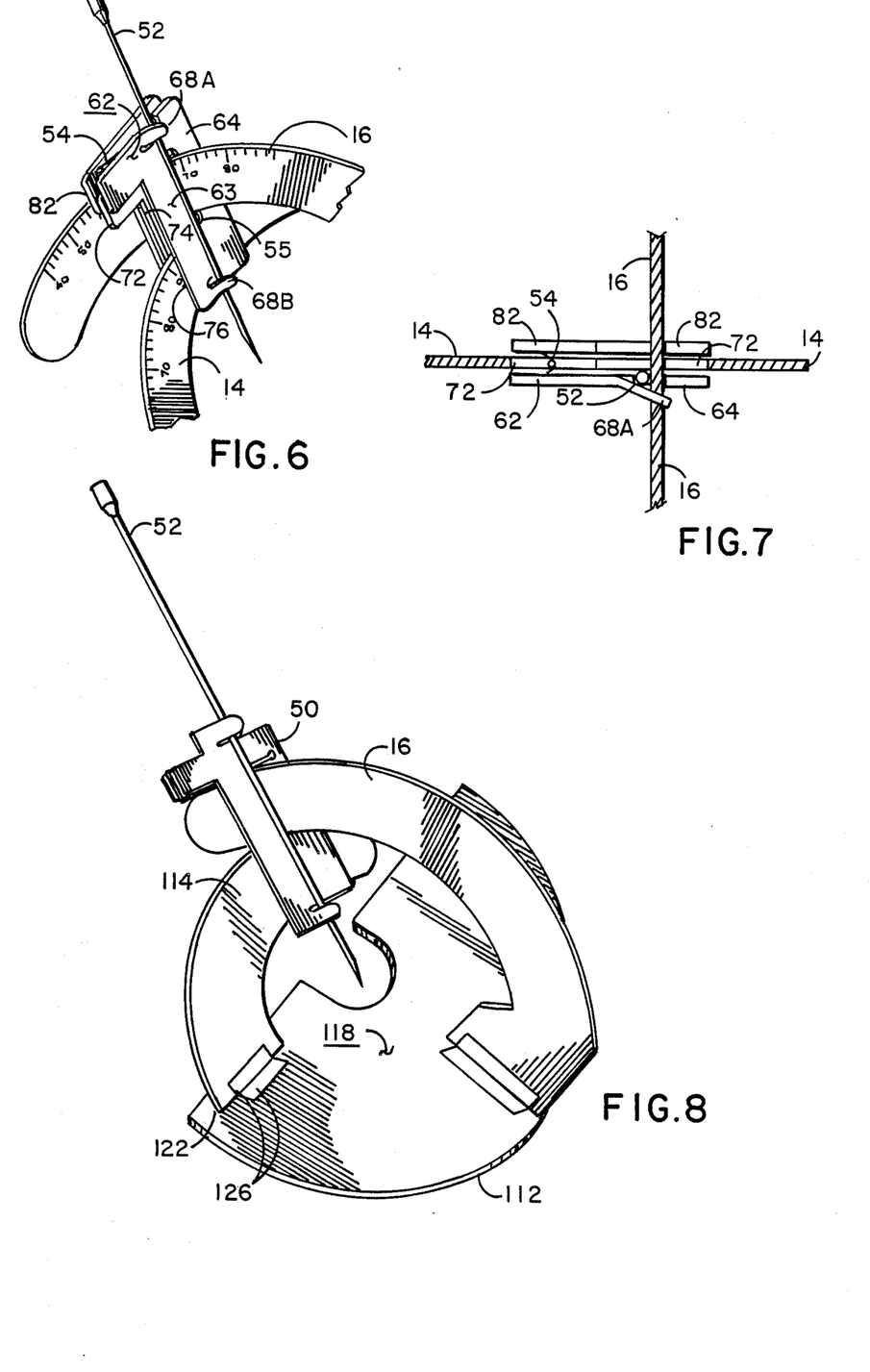
FIG. 6 is a detailed perspective view of the combined coupling bracket and needle holder on the primary and secondary members of the embodiment illustrated by FIG. 5.
FIG. 7 is an overhead view of the combined coupling bracket and needle holder on the primary and secondary members of the embodiment illustrated by FIG. 5.
FIG. 8 is a perspective view of another embodiment comprising the present invention in the fully erect, self-supporting state.

The erected, self-supporting angulator device 10 complete with combination coupling bracket and needle holder 50 is illustrated by FIGS. 5, 6, and 7. The primary member 14 rotatably joined to the surfae 18 of the base plate 12 has been elevated and the combination coupling bracket and needle holder 50 slidably mounted on the thickness of the support member 14. Clearly, the thickness of the primary member 14 passes through the broad space 76 of the middle plate 70. By compressing the L-shaped arm 72 towards the L-shaped arms 62 and 82 of the bracket 50, the gap 90 is widened and the bracket 50 then can be slided over the entirety of the primary member 14 until another desired position is achieved. The secondary member 16 has also been elevated from the folded state and the end 32 inserted into and passed through the slot 55 of the coupling bracket 50. As shown by FIGS. 5, 6, and 7, as the coupling bracket and needle holder 50 is slid over the surface of the primary member 14, the secondary member 16 will also rotate conform to any desired position on the arch; and thus maintain a variety of different angles of intersection with the primary member. In a similar fashion, the coupling bracket 50 can be slid over the secondary member 16 and the primary member 14 will follow. It is clear, therefore, that with each change of position for the coupling bracket and needle holder 50 on the primary member 14, there will be a different angle of intersection achieved for the members 14 and 16 over a range of substantially 180° in any direction.

In its intended use with human or animal subjects, it is expected that the base plate 12 will be positioned on the skin of the subject at an insertion site overlying the tissue to be localized and/or examined. The center of the apertue 20 typically, will be positioned such that the needle point is situated directly over the planned site of skin penetration. The adhesive 38 will maintain the general position of the angulator device 10 on the skin of the subject without discomfort to the patient. The flexibility of the base plate material allows for movement through breathing or involuntary muscle contraction for the subject without loss of positioning for the angulator. Once the base plate has been attached to the skin surface, the L-shaped arms 82 and 62 are squeezed against the L-shaped arm section 72. The combination coupling bracket and needle holder 50 can now be moved along both arched members in any direction between 0° and 180° (preferably between 30°-150°) relative to the skin surface and then secured into place. As a convenience, angle degree markings can be printed on the surface of the primary and secondary members to serve as reference points as seen in FIG. 6. Once secured into position, the needle retained by clips 68a and 68b can be checked using the imaging system for the desired precise location and angle of insertion. Any necessary adjustments can be made before the needle or other object is advanced into the tissues along the preselected axis. Once it is decided to advance the needle into the tissues of the subject, the angulator will continue to aim and hold the needle securely while it is being advanced into the tissues; since biopsy needles and the like are generally from .4 to 8 inches in length, the needle may be advanced into the tissues until approximately 3½ inches of the needle's shaft remain exposed to view. If deeper penetration is desired, this may then be accomplished by releasing the needle from the coupling bracket and folding the arched members 14, 16 and coupling bracket 50 flat against the skin of the patient. The needle is then held in position by the tissues themselves and it may then be advanced further until the desired degree of penetration is achieved. The base plate and collapsed arched members will not interfere with the surgeon's hands while the biopsy or aspiration samples are being taken; or while any other surgical function or procedure is being carried out. After the surgical procedure has been completed, the angulator device 10 may be easily peeled off the skin and discarded either before or after the needle has been withdrawn from the tissues.

It should be noted that the present invention as illustrated by the preferred embodiments of FIGS. 1-7 has many desirable advantageous features and uses which fall into any of three general categories: First, the ease of use is apparent and highly desirable: The base plate of the angulator device may be easily attached to the skin of the subject by adhesive or other retention means and can be easily removed at the end of any surgical procedure. The angulator may be mounted or positioned on any horizontal, oblique, or even vertical skin surface. The angulator device is foldable and may be erected for use in a matter of seconds. The design and base are adaptable to almost any body contour and many envisioned surgical procedures. The angulator device and preferred coupling bracket will accept a variety of different objects of varying sizes, lengths and diameters commonly in clinical use. The device frees the surgeon's hands for other functions thereby often eliminating the need for an assistant. Moreover, the angulator device allows the needle or other object to be inserted to be easily disconnected from the remainder of the apparatus at any time; and allows the remainder to be folded flat against the skin or quickly removed entirely thereby eliminating obstacles and obstructions to the surgical procedure itself.

Second, the accuracy provided by the angulator devices comprising the present invention is clearly more precise and easily verified than any other apparatus presently known to date: The needle or other object to be inserted is held securely at precisely the exact angle of insertion desired relative to the patient's body; the traditional balancing and support attempts using towels, gauze pads, or other conveniences becomes unnecessary and obsolete. The angle of insertion can be easily readjusted when and if necessary without difficulty. The needle or object to be inserted can be aimed at the desired target at the preferred angle of inclination over a broad range of angles with great precision and reliability. Angle degree scales may be provided along the surface of the individual members as reference points. The needle to be inserted and the angulator device (once attached to the skin of the patient) adjust and move with the motions of the patient so that the needle position is unaffectd with respect to the target tissue. Patient immobilization requirements are therefore greatly reduced or in some instances, can be eliminated altogether.

Third, the angulator and its uses are adaptable to all conventionally known imaging systems: The angulator may be used with X-ray fluoroscopy, computerized tomography, ultrasound, magnetic resonance and the like. If desired, small radiopaque centering wires can be built into the base plate of the device to identify the focal point at which the needle will enter the skin. The angulator allows the patient to be moved into and out of any imaging system without fear of disturbing or altering the position of the needle. Morever, the surgeon's hands are kept out of the radiation field when fluoroscopy or computerized tomography imaging systems are utilized. Lastly, it is clear that in preferred formats, the angulator will be prepared conveniently as a pre-sterilized article which is disposable and constructed such that it may be erected and then subsequently collapsed with a minimum of effort.

Figure 9:
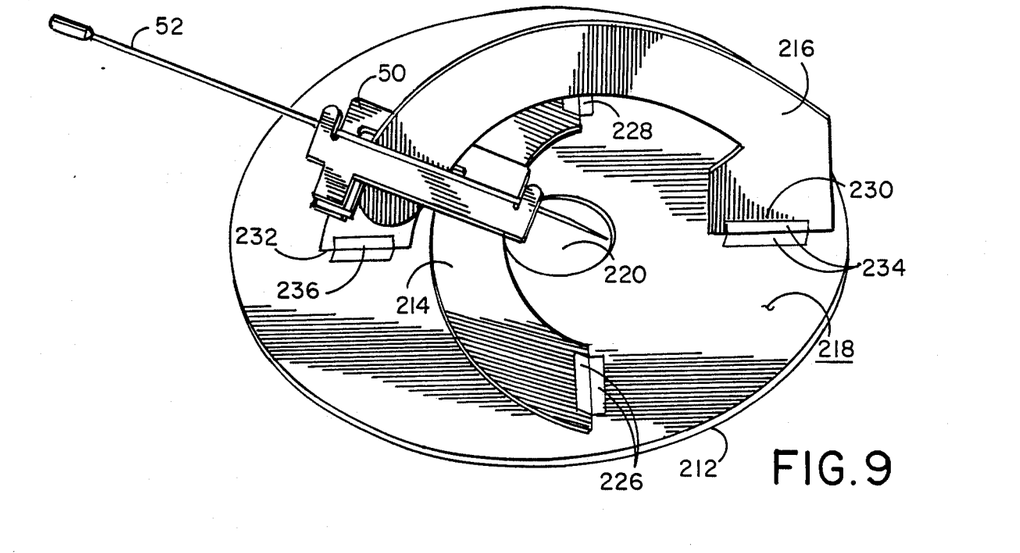
FIG. 9 is a perspective view of another embodiment comprising the present invention in the fully erect, self-supporting state.
Figure 10:
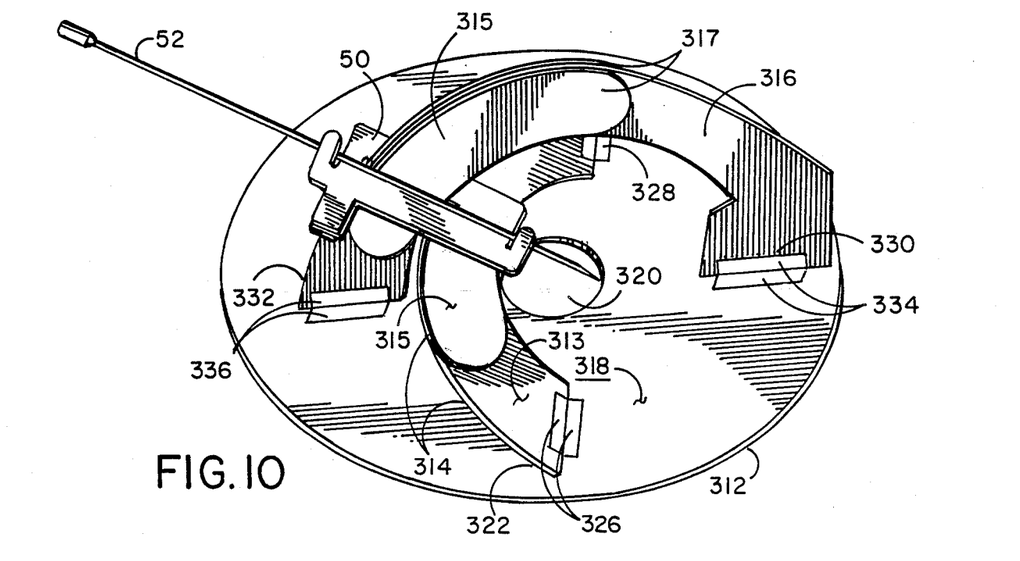
FIG. 10 is a perspective view of another embodiment of the present invention in the fully erect, self-supporting state.

A non-exhaustive, representative showing of other useful embodiments of the present invention in general are illustrated by FIGS. 8, 9 and 10 respectively. The embodiment of FIG. 8 shows the primary member 114 to be an arched construct rotatably joined to the surface 18 of the base plate 12 only at one end 122. The manner of rotatable juncture is again via a hinge 126, although any other means for rotatably joining the primary member 114 to the base plate 12 is equally useful and suitable. All other components of the angulator device are as previously described herein.

Another, perhaps less preferred, embodiment of the present invention is seen in FIG. 9 in which the adjacently positioned secondary member 216 is configured as an arched construct having two ends 230 and 232 respectively. Each end 230, 232 is rotatably joined to a substantially circular base plate 212 containing a substantially oval shaped aperture 220 at the center. As before, the preferred means for rotatably joining the secondary member 216 and the primary member 214 to the surface 218 of the base plate 212 is via a series of hinges 226, 228, 234, and 236 respectively. Each of the other components comprising the embodiment of FIG. 8 are as previously described herein.

Finally, the alternate embodiment shown by FIG. 10 illustrates the situation wherein the primary member 314 is composed of two individual arched elements 313, 315, each of which is rotatably joined at their respective ends 322, 324 to the surface 318 of a circular base plate 312 having an oval aperture 320 at its center. Similarly, the adjacently positioned secondary member 316 is composed of two individual arched components 315, 317 whose respective ends are rotatably joined to the base plate 312. In this embodiment also, a series of hinges 326, 328, 334, and 336 join each respective component end 322, 324, 330, and 332 to the surface 318 of the base plate 312. Each of the other elements in this embodiment are as previously described herein.

The present invention is not to be restricted in form nor limited in scope except by the claims appended hereto.

What I claim is:

1. A folded angulator erectable on demand into a self-supporting device useful for precise positioning and percutaneous insertion of an object into a subject, said folded angulator comprising:
- a flexible base plate having a plurality of external surfaces, said base plate being positionable at will on the body of the subject;
- at least one primary member rotatably hinged at a primary position to said base plate and rotatably extendable at a range of about 180 degrees over said base plate;
- at least one secondary member rotatably hinged to said base plate at a secondary position which is substantially spatially removed from said primary position on said base plate, said secondary member being rotatably extendable at a range of about 180 degrees over said base plate for intersection with said primary member at a plurality of different angles of intersection over about a 180 degree range;
- means for coupling said secondary member to said primary member over the 180 degree range at a plurality of different angles of intersection;
- means for holding the object to be inserted upon at least one of said members after said primary and secondary members are coupled at a desired angle of intersection; and
- an adhesive disposed upon an external surface of said flexible base plate for securing said base plate to the body of the subject at a desired position.

2. An erected, self-supporting angulator collapsable on demand and useful for precise positioning and percutaneous insertion of an object into a subject, said erected angulator comprising:
- a flexible base plate having a plurality of external surfaces, said base plate being positionable at will on the body of the subject;
- at least one primary member rotatably hinged at a primary position to said base plate and rotatably extended at a range of about 180 degrees over said base plate;
- at least one secondary member rotatably hinged to said base plate at a secondary position which is substantially spatially removed from said primary position on said base plate, said secondary member being rotatably extended at a range of about 180 degrees over said base plate for intersection with said primary member at a plurality of different angles of intersection over about a 180 degree range;
- means for coupling said secondary member to said primary member over the 180 degree range at a plurality of different angles of intersection;
- means for holding the object to be inserted upon at least one of said members after said primary and secondary members coupled at a desired angle of intersection; and
- an adhesive disposed upon an external surface of said flexible base plate for securing said base plate to the body of the subject at a desired position.

3. The angulator as recited in claim 2 wherein the object to be inserted is maintained by said holding means at a position substantially perpendicular to and isocentric with the plane of intersection formed by said members.

4. The angulator as recited in claim 1 or 2 wherein said base plate further comprises at least one aperture.

5. The angulator as recited in claim 1 or 2 wherein said primary member is arched in configuration.

6. The angulator as recited in claim 1 or 2 wherein said secondary member is arched in configuration.

7. The angulator as recited in claim 1 or 2 wherein said members are rotatably joined to said base plate by hinges.

8. The angulator as recited in claim 1 or 2 wherein said seondary member is rotatably joined to said base plate along a line which is substantially perpendicular to the line formed by the joining of said rotatably joined primary member on said base plate.

* * * * *